(12) United States Patent
Stössel et al.

(10) Patent No.: US 8,039,126 B2
(45) Date of Patent: Oct. 18, 2011

(54) MATERIALS FOR ORGANIC ELECTROLUMINESCENT DEVICES

(75) Inventors: Philipp Stössel, Frankfurt am Main (DE); Holger Heil, Darmstadt (DE); Arne Buesing, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 616 days.

(21) Appl. No.: 12/295,459

(22) PCT Filed: Mar. 3, 2007

(86) PCT No.: PCT/EP2007/001839
§ 371 (c)(1),
(2), (4) Date: Sep. 30, 2008

(87) PCT Pub. No.: WO2007/115610
PCT Pub. Date: Oct. 18, 2007

(65) Prior Publication Data
US 2009/0058289 A1 Mar. 5, 2009

(30) Foreign Application Priority Data

Apr. 1, 2006 (DE) .................. 10 2006 015 183

(51) Int. Cl.
*H01L 51/54* (2006.01)
(52) U.S. Cl. ........ 428/690; 428/917; 313/504; 313/505; 313/506; 257/E51.026; 564/426
(58) Field of Classification Search ................... 428/690, 428/917; 313/504, 505; 257/E51.026; 564/426
See application file for complete search history.

(56) References Cited

FOREIGN PATENT DOCUMENTS

EP 0 786 926 A2 7/1997
WO WO 2006/000388 A1 1/2006

OTHER PUBLICATIONS

Grutzmacher et. al., Chiral Phosphane Alkenes(PALS):Simple Synthesis . . . ,2006, Chem. Eur. J., vol. 12, pp. 5849-5858.*

* cited by examiner

*Primary Examiner* — D. Lawrence Tarazano
*Assistant Examiner* — Gregory Clark
(74) *Attorney, Agent, or Firm* — Connolly Bove Lodge & Hutz LLP

(57) ABSTRACT

The present invention relates to triarylamines which are substituted by defined groups. These compounds can be used for producing organic electroluminescent devices.

20 Claims, No Drawings

MATERIALS FOR ORGANIC ELECTROLUMINESCENT DEVICES

RELATED APPLICATIONS

This application is a national stage application (under 35 U.S.C. §371) of PCT/EP2007/001839, filed Mar. 3, 2007, which claims benefit of German Patent Application No. 10 2006 015 183.6, filed Apr. 1, 2006.

The present invention relates to arylamines, to the use thereof for the production of organic electroluminescent devices, and to organic electroluminescent devices comprising these compounds.

The general structure of organic electroluminescent devices which comprise semiconducting organic compounds and are capable of the emission of light in the visible spectral region is described, for example, in U.S. Pat. No. 4,539,507, U.S. Pat. No. 5,151,629, EP 0676461 and WO 98/27136. However, these devices still have considerable problems which require urgent improvement for use in high-quality displays. Thus, in particular, the operating lifetime in the case of blue emission is still inadequate, meaning that it has to date only been possible to implement simple applications commercially. In addition, the blue emitters usually used do not have adequate thermal stability.

JP 04-184892 describes distilbenamines, tristilbenamines and further stilbene derivatives as emitting compounds for OLEDs. The devices comprising the proposed compounds do not have satisfactory lifetimes. In addition, the thermal stability of these compounds during device production by vacuum sublimation is inadequate. The decomposition products result in contamination of the electroluminescent device and thus in poorer electronic properties. In addition, other stilbenamines, as used in accordance with the prior art (for example in accordance with JP 08-239655 or EP 1167488), only have inadequate thermal stability.

WO 06/000388 describes aryl-substituted tristilbenamines as emitting compounds for OLEDs. The devices comprising the proposed compounds exhibit pale-blue, but not dark-blue emission.

In general, it is noted in the case of stilbenamines that they exhibit undesired side reactions at high temperature, as used during sublimation for the purification of the materials and during device production (scheme 1). Thus, these compounds exhibit thermally induced cis/trans isomerisation. Cis-stilbenamine is able to react further in an intramolecular ring-closure reaction to give the corresponding dihydrophenanthrene and in the presence of an oxidant, for example residues of oxygen, to give the corresponding phenanthrene. This results in inhomogeneous material mixtures in the OLED, which makes reproducible device production more difficult. Furthermore, a thermally induced olefin metathesis reaction is generally observed. This results on the one hand in low-molecular-weight compounds, which lead to contamination of the OLED, and on the other hand in a high-molecular-weight resinified residue since the metathesis reaction results in crosslinking of the material in the case of a plurality of stilbene groups in the molecule. This resinified residue results in a considerable loss of material in the case of many materials. In addition, relatively high-molecular-weight vapour-deposited material formed by olefin metathesis results in longer-wave emission since these compounds have a more widely extended π-electron system.

Scheme 1:

1) Thermally induced trans/cis isomerisation

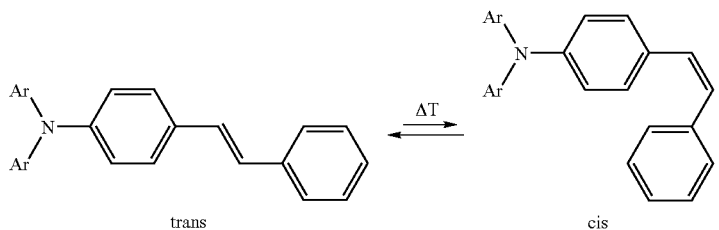

trans          cis

2) Dihydrophenanthrene and phenanthrene formation

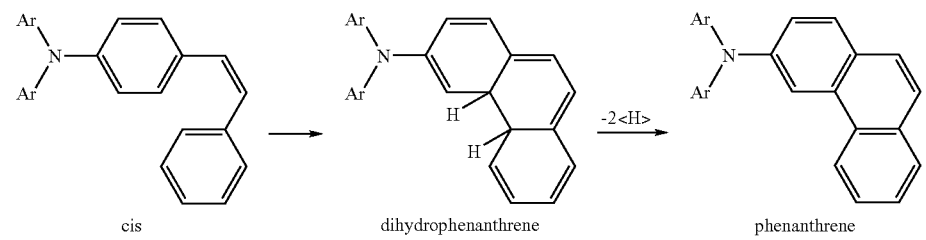

cis          dihydrophenanthrene          phenanthrene

3) Thermally induced olefin methathesis

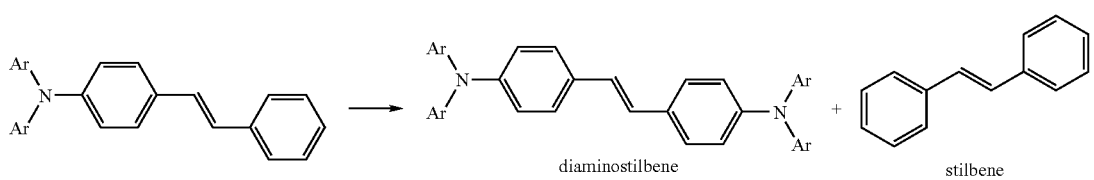

diaminostilbene          stilbene

The object of the present invention was therefore to offer improvements for this purpose, in particular compounds having an improved lifetime at the same time as improved dark-blue colour coordinates and high thermal stability.

Surprisingly, it has been found that organic electroluminescent devices which comprise triarylamine derivatives which are substituted by dibenzosuberene, dibenzooxepine, dibenzoazepine or derivatives of these compounds in the emitting layer exhibit significant improvements compared with the prior art. Using these materials, improved lifetimes at the same time as dark-blue emission colour and good efficiency are obtained. Furthermore, these materials have higher thermal stability than the stilbenamines used as blue-emitting compounds in accordance with the prior art. The present invention therefore relates to these compounds and to the use thereof in OLEDs, in particular in the emitting layer.

The invention relates to compounds of the formula (1)

$R^1$ is on each occurrence, identically or differently, H or a hydrocarbon radical having 1 to 20 C atoms, which may be aliphatic or aromatic or a combination of aliphatic and aromatic; one or more H atoms here may also be replaced by F; two or more radicals $R^1$ here may also form a mono- or polycyclic, aliphatic or aromatic ring system with one another;

n is 0, 1, 2 or 3;

m is, identically or differently on each occurrence, 0 or 1, where m=0 means that the group Y is not present and instead radicals R are bonded in these positions.

For the purposes of this invention, an aryl group or heteroaryl group is taken to mean an aromatic group or heteroaromatic group having a common aromatic π-electron system. For the purposes of this invention, this may be a

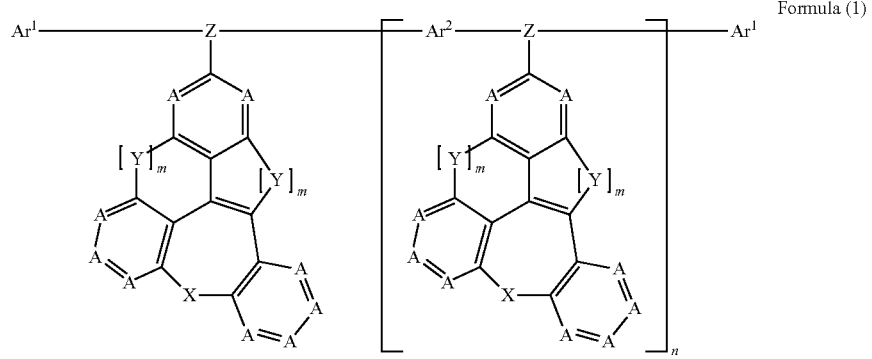

Formula (1)

where the following applies to the symbols and indices used:

Z is, identically or differently on each occurrence, N, P, As or P=O;

X, Y are, identically or differently on each occurrence, $CR_2$, C=O, O, S, NR, $SiR_2$, PR, P(=O)R, S(=O) or $SO_2$;

A is, identically or differently on each occurrence, CR or N;

$Ar^1$ is, identically or differently on each occurrence, a monovalent aromatic or heteroaromatic ring system having 5 to 40 aromatic ring atoms, which may be substituted by one or more radicals R;

$Ar^2$ is, identically or differently on each occurrence, a divalent aromatic or heteroaromatic ring system having 5 to 40 aromatic ring atoms, which may be substituted by one or more radicals R;

R is, identically or differently on each occurrence, H, F, Cl, Br, I, CN, $NO_2$, $Si(R^1)_3$, $N(R^1)_2$, $B(OR^1)_2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^1$, where one or more non-adjacent $CH_2$ groups may be replaced by —$R^1$C=C$R^1$—, —C≡C—, $Si(R^1)_2$, $Ge(R^1)_2$, $Sn(R^1)_2$, C=O, C=S, C=Se, C=N$R^1$, —O—, —S—, —N($R^1$)— or —CON$R^1$— and where one or more H atoms may be replaced by F, Cl, Br, I, CN or $NO_2$, or an aromatic or heteroaromatic ring system having 5 to 40 aromatic ring atoms, which may be substituted by one or more radicals $R^1$, or an aryloxy or heteroaryloxy group having 5 to 24 aromatic ring atoms, which may be substituted by one or more radicals $R^1$, or a combination of two, three, four or five of these systems; two or more substituents R here may also form a mono- or polycyclic, aliphatic or aromatic ring system with one another;

simple homo- or heterocycle, for example benzene, pyridine, thiophene, etc., or it may be a condensed aromatic ring system, in which at least two aromatic or heteroaromatic rings, for example benzene rings, are "fused" to one another, i.e. are condensed onto one another by anellation, i.e. have at least one common edge and consequently also a common aromatic πelectron system. These aryl or heteroaryl groups may be substituted or unsubstituted; likewise, any substituents present may form further ring systems. Thus, for example, systems such as naphthalene, anthracene, phenanthrene, pyrene, etc., are regarded as aryl groups and quinoline, acridine, benzothiophene, carbazole, etc., as heteroaryl groups for the purposes of this invention, while, for example, biphenyl, fluorene, spirobifluorene, etc., do not represent aryl groups since they involve separate aromatic π-electron systems.

For the purposes of this invention, an aromatic ring system contains 6 to 30 C atoms in the ring system. For the purposes of this invention, a heteroaromatic ring system contains 2 to 30 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom, or in which one or more aryl or heteroaryl groups are condensed onto a non-aromatic cyclic group. Thus, for example, a plurality of mutually linked aromatics, such as, for example, biphenyl, or also systems such as 9,9'-spirobifluorene, 9,9-diarylfluorene, triarylamine, diaryl ethers, etc., are intended to be taken to mean aromatic ring systems for the purposes of this invention. Likewise, systems such as dibenzosuberene, dibenzooxepine, dibenzoazepine, etc. are taken to mean aromatic ring systems for the purposes of this invention.

For the purposes of this invention, a cyclic alkyl group is taken to mean both monocyclic and also bi- and polycyclic alkyl groups.

For the purposes of the present invention, a $C_1$- to $C_{40}$-alkyl group, in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methyl-butyl, n-pentyl, s-pentyl, cyclopentyl, n-hexyl, cyclohexyl, n-heptyl, cyclo-heptyl, n-octyl, cyclooctyl, 2-ethylhexyl, adamantyl, trifluoromethyl, penta-fluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5 to 40 aromatic ring atoms, which may also in each case be substituted by the above-mentioned radicals R or $R^1$ and which may be linked to the aromatic or heteroaromatic via any desired positions, is taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, truxene, isotruxene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole, triphenylamine, naphthyldiphenylamine, dinaphthylphenylamine, diphenyl ether, dibenzosuberene, dibenzooxepine, dibenzoazepine and combinations of these systems.

Preferred embodiments of compounds of the formula (1) are described below.

In a preferred embodiment of the invention, the symbol Z, identically or differently on each occurrence, stands for N or P=O. In a particularly preferred embodiment of the invention, the symbol Z stands for N.

In a preferred embodiment of the invention, a maximum of one symbol A in each aromatic ring stands for N, and the other symbols A in this aromatic ring stand for CR. In a particularly preferred embodiment of the invention, the symbol A stands for CR.

In a preferred embodiment of the invention, at least one group $Ar^1$ stands for a group of the formula (2)

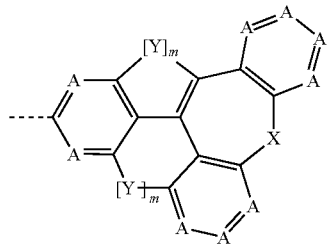

Formula (2)

where the symbols and indices have the same meaning as described above, and the dashed bond denotes the link to the group Z. A maximum of one symbol A in each aromatic ring here preferably stands for N and the other symbols A in this aromatic ring stand for CR; the symbol A particularly preferably stands for CR.

Particular preference is given to compounds of the formula (1a)

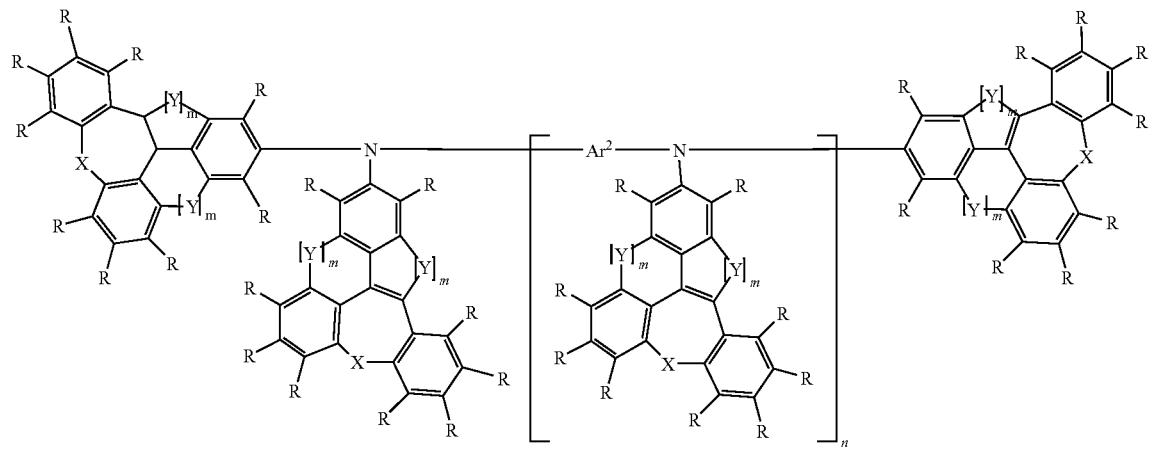

Formula (1a)

where the symbols and indices have the same meaning as described above.

Preference is furthermore given to compounds of the formulae (1) and (1a) in which the symbol X, identically or differently on each occurrence, stands for $CR_2$, O, NR or $SiR_2$. Particular preference is given to compounds of the formulae (1) or (1a) in which the symbol X, identically or differently on each occurrence, stands for $CR_2$ or O.

If the symbol X stands for a group of the formula $CR_2$, R in the unit $CR_2$ then preferably stands, identically or differently on each occurrence, for a straight-chain alkyl group having 1 to 4 C atoms or a branched alkyl group having 3 or 4 C atoms, where in each case one or more H atoms may be replaced by F, or for an aryl or heteroaryl group having 5 to 10 aromatic ring atoms, or a combination of two or three of these systems; the two radicals R in the group $CR_2$ here may also form a mono- or polycyclic, aliphatic or aromatic ring system with one another and thus construct a spiro system. Particularly preferred radicals R are methyl, tert-butyl, phenyl, ortho-tolyl, para-tolyl or para-tert-butylphenyl. Two phenyl groups here may in each case also form a ring system with one another and thus construct a spiro system, as shown in formula (3) for the skeleton of dibenzosuberene:

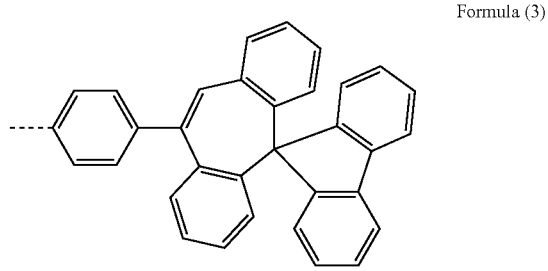

Formula (3)

Preference is furthermore given to compounds of the formulae (1) and (1a) in which the symbol Y, identically or differently on each occurrence, stands for $CR_2$, O, NR or $SiR_2$. Particular preference is given to compounds of the formulae (1) and (1a) in which the symbol Y, identically or differently on each occurrence, stands for $CR_2$ or O.

Preference is furthermore given to compounds of the formulae (1) and (1a) in which the symbol R which is not bonded to the group X stands, identically or differently on each occurrence, for H, F, $Si(R^1)_3$, $B(OR^1)_2$, a straight-chain alkyl or alkoxy group having 1 to 6 C atoms or a branched or cyclic alkyl or alkoxy group having 3 to 10 C atoms, where in each case one or more $CH_2$ groups may be replaced by $-R^1C=CR^1-$, $Si(R^1)_2$, $-O-$, $-S-$ or $-N(R^2)-$ and where in each case one or more H atoms may be replaced by F, or for an aryl or heteroaryl group having 5 to 14 aromatic ring atoms, or a combination of two or three of these systems; two or more adjacent radicals R here may also form a mono- or polycyclic, aliphatic or aromatic ring system with one another. Particularly preferred radicals R are selected from the group consisting of H, F, $Si(R^1)_3$, $B(OR^1)_2$, straight-chain alkyl groups having 1 to 4 C atoms, branched alkyl groups having 3 to 5 C atoms or cyclic alkyl groups having 5 to 10 C atoms, where in each case one or more H atoms may be replaced by F, or monovalent aryl or heteroaryl groups having 6 to 10 aromatic ring atoms, or a combination of two of these systems.

Preference is furthermore given to compounds of the formula (1b)

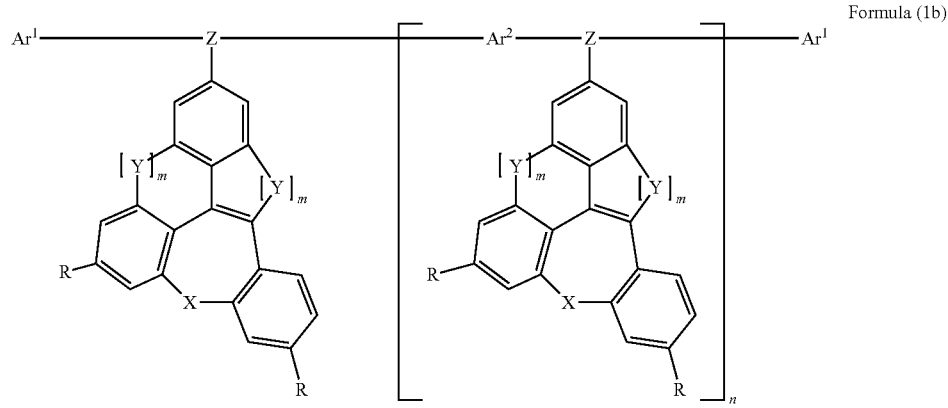

Formula (1b)

where the symbols and indices have the same meaning as described above.

Preference is furthermore given to compounds of the formulae (1) and (1a) and (1b) in which the symbol $Ar^2$, identically or differently on each occurrence, stands for an aromatic or heteroaromatic ring system having 6 to 24 aromatic ring atoms. The symbol $Ar^2$, identically or differently on each occurrence, particularly preferably stands for an aryl, heteroaryl or biaryl group having 6 to 16 aromatic ring atoms or for an R-substituted or unsubstituted fluorene, spirobifluorene or indenofluorene.

Preference is furthermore given to compounds of the formulae (1) and (1a) and (1b) in which the index n stands for 0, 1 or 2, particularly preferably for 0 or 1, very particularly preferably for 0.

Preference is furthermore given to compounds of the formulae (1) and (1a) and (1b) in which at most one index m on each unit of the formula (2) is equal to 1. Particular preference is given to compounds of the formulae (1) and (1a) in which all indices m are equal to 0.

Particular preference is thus given to compounds of the formula (1c)

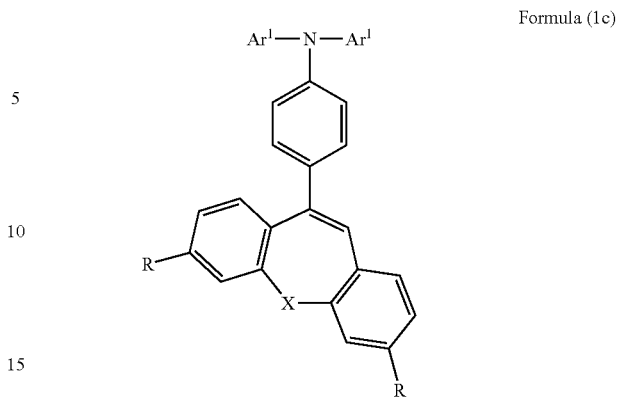

where the symbols have the same meaning as described above, and in which the symbol Ar¹ preferably represents a group of the formula (2) depicted above.

Preference is furthermore given to compounds of the formulae (1) and (1a) to (1c) in which all groups X are selected identically and all groups Y, if present, are selected identically and in which the groups are also in each case identically substituted, i.e. symmetrical compounds. Particular preference for n=0 is given to compounds which have a three-fold axis of symmetry.

Examples of preferred compounds of the formulae (1) and (1a) to (1c) are the compounds (1) to (33) depicted below.

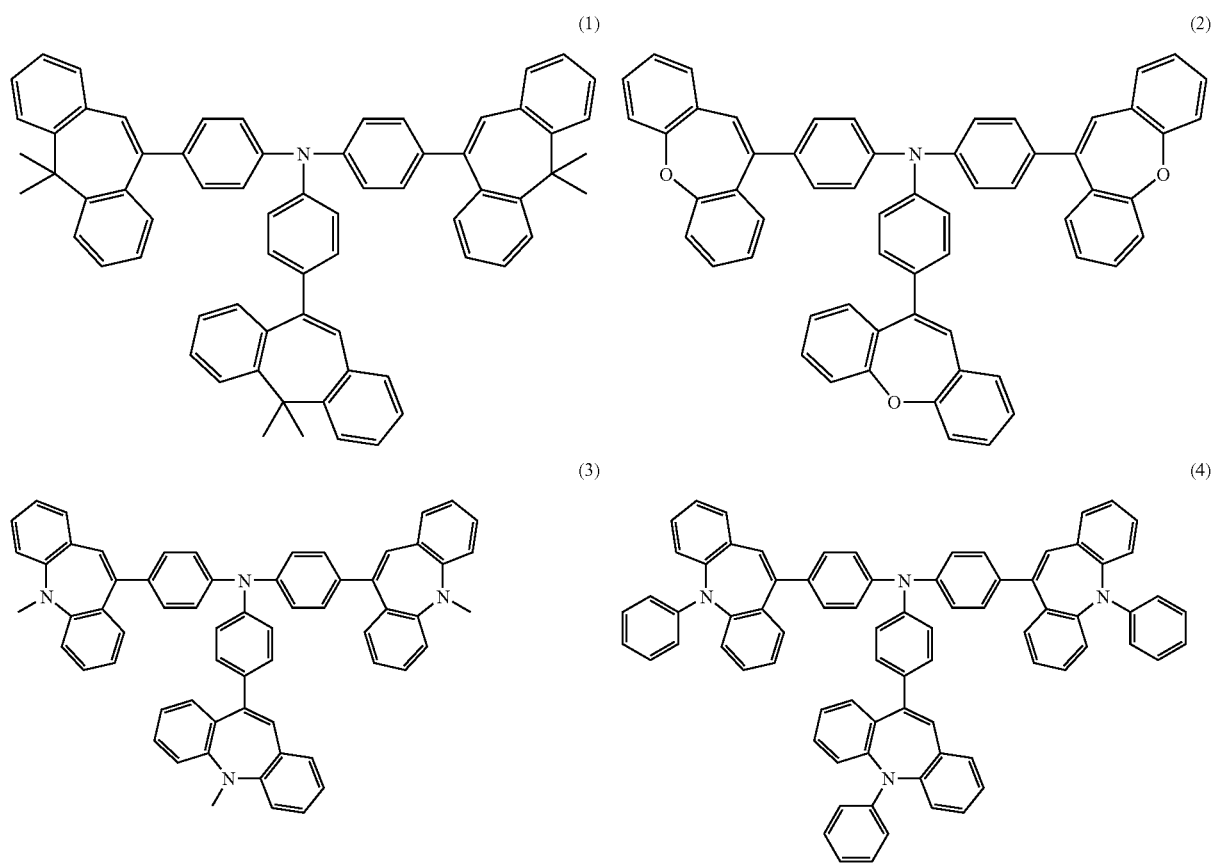

-continued
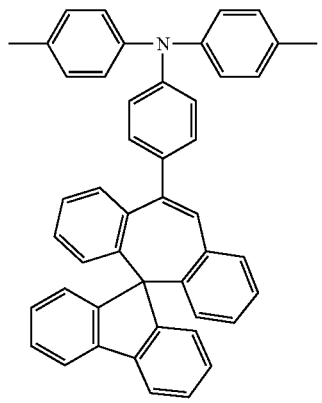
(5)
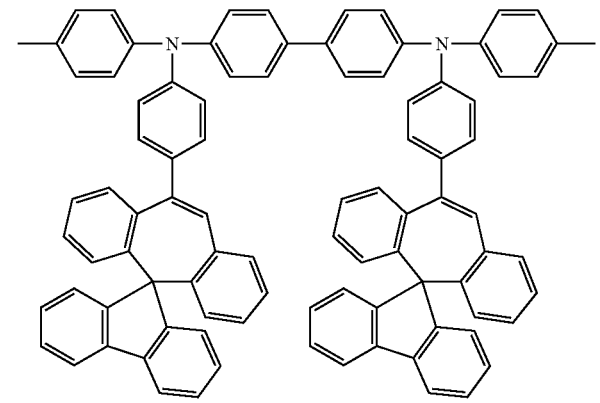
(6)
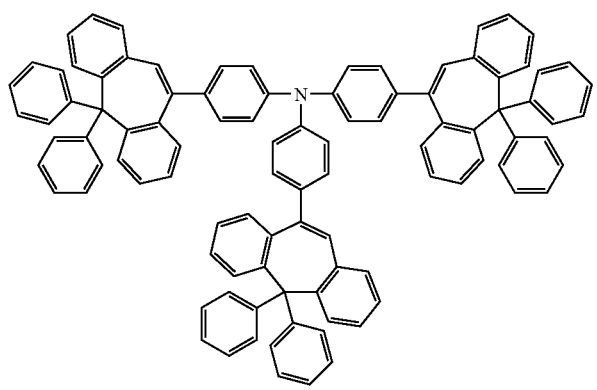
(7)
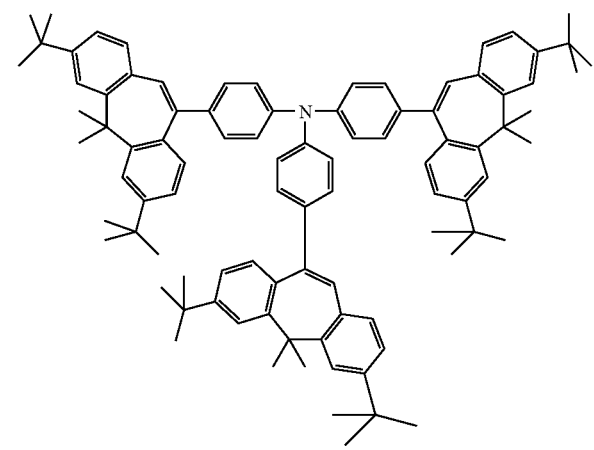
(8)
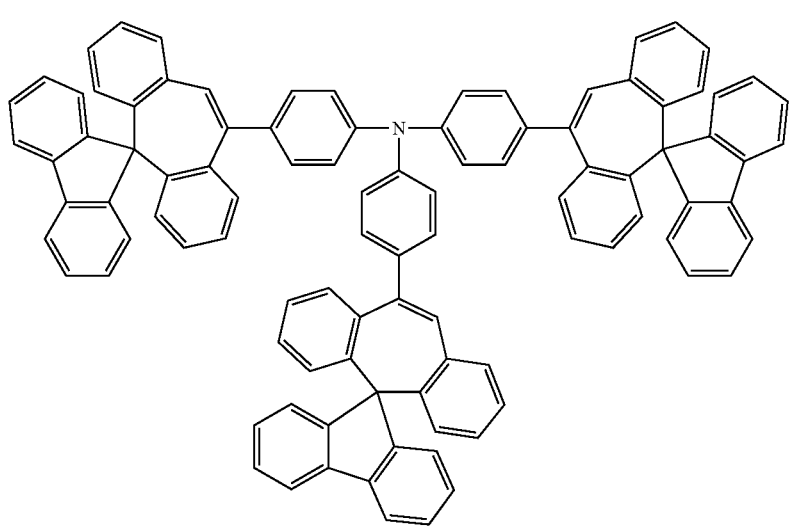
(9)
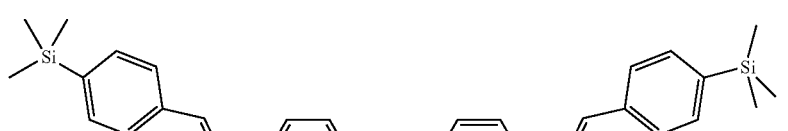
(10)

The compounds according to the invention described above can also be used, for example, as comonomers for the preparation of corresponding conjugated, partially conjugated or non-conjugated polymers, oligomers or also as the core of dendrimers. Particularly suitable for this purpose are halogenated compounds, in which case the polymerisation preferably takes place via the halogen functionality.

The invention thus furthermore relates to conjugated, partially conjugated and non-conjugated polymers, oligomers or dendrimers comprising one or more compounds of the formula (1), where one or more radicals R represent bonds from the compound of the formula (1) to the polymer or dendrimer.

These polymers may contain further recurring units. These further recurring units are preferably selected from the group consisting of fluorenes (for example in accordance with EP 842208 or WO 00/22026), spirobifluorenes (for example in accordance with EP 707020, EP 894107 or WO 06/061181), triarylamines, para-phenylenes (for example in accordance with WO 92/18552), carbazoles (for example in accordance with WO 04/070772 and WO 04/113468), thiophenes (for example in accordance with EP 1028136), dihydrophenanthrenes (for example in accordance with WO 05/014689), indenofluorenes (for example in accordance with WO 04/041901 and WO 04/113412), aromatic ketones (for example in accordance with WO 05/040302), phenanthrenes (for example in accordance with WO 05/104264) and/or metal complexes, in particular orthometallated iridium complexes. It should expressly be pointed out here that the polymers may also have a plurality of different recurring units which are selected from one or more of the above-mentioned groups.

The compounds are synthesised by methods of organic chemistry which are familiar to the person skilled in the art. Thus, for example, dibenzosuberene (Schmuck et al., *Synthesis* 2002, 5, 655), 5,5'-dimethyldibenzosuberene (Vinatoru et al., *Org. Prep. Proced. Int.* 1975, 7(2), 98), dibenzooxepine (Hess et al., *J. Am. Chem. Soc.* 1967, 89(11), 2746) and N-methyldibenzoazepine (Ohta et al, *Chem. Pharm Bull.* 1981, 29(5), 1221) and corresponding substituted derivatives can be synthesised by literature methods. Innumerable further derivatives of the above-mentioned parent structures have been described in the literature and play a role, in particular, as pharmaceutical intermediates. These compounds can then be reacted, for example in a Heck coupling, with a triarylamine which is substituted on at least one aryl group by chlorine, bromine, iodine or another leaving group, such as, for example, sulfonate, for example with tris(parabromophenyl)amine (scheme 2).

Scheme 2:

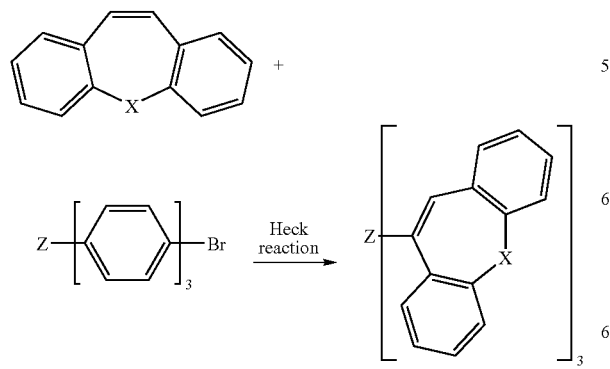

$X = CR_2$, O, NR, etc.
$Z = N, P, P = O, As$

Alternatively, addition of bromine to the double bond, followed by elimination of HBr, subsequent conversion of the vinyl bromide into the corresponding boronic acid and final Suzuki coupling is possible (scheme 3). The boronic acid here is preferably not isolated, but instead is prepared in situ and employed directly for the Suzuki coupling. A suitable ligand for the palladium in the Suzuki coupling here is, in particular, tris(1-furyl)phosphine.

Scheme 3:

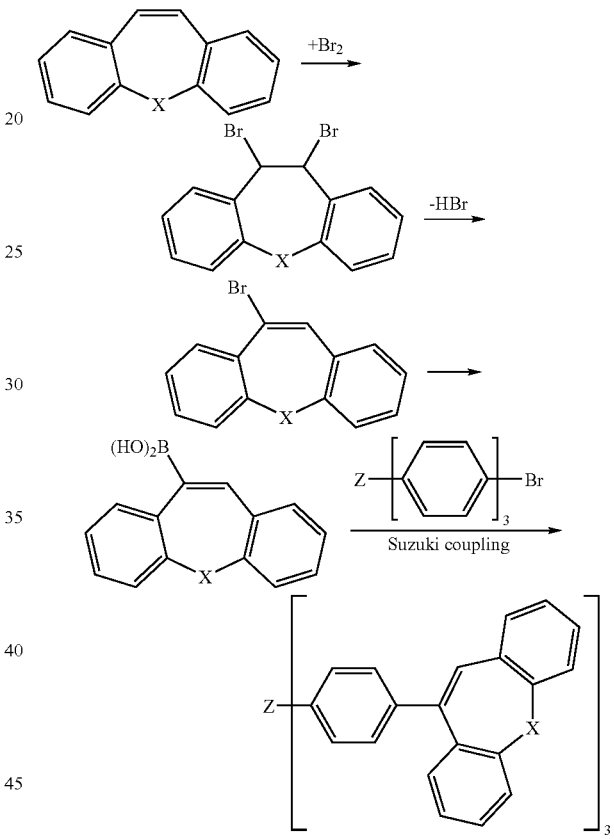

$X = CR_2$, O, NR, etc.
$Z = N, P, P = O, As$

The present invention therefore furthermore relates to a process for the preparation of compounds of the formula (1), characterised in that a boronic acid derivative of the formula (4)

Formula (4)

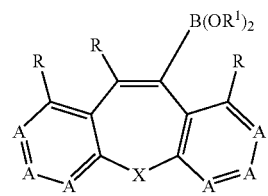

where the symbols have the meaning given above, is reacted in a Suzuki coupling with the central unit of the compound of the formula (1) which contains chlorine, bromine, iodine, triflate, tosylate or $OSO_2R^1$ as reactive group, where $R^1$ has the same meaning as described above.

The compounds of the formula (1) can be used in organic electronic devices, in particular in organic electroluminescent devices.

The invention therefore furthermore relates to the use of compounds of the formula (1) in organic electronic devices, in particular in organic electroluminescent devices.

The invention furthermore relates to organic electronic devices comprising at least one organic layer, characterised in that the organic layer comprises at least one compound of the formula (1).

The organic electronic device is preferably selected from organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), organic photo receptors, light-emitting electrochemical cells (LECs) and organic laser diodes (O-lasers). Particular preference is given to organic electroluminescent devices (OLEDs, PLEDs).

The organic electroluminescent device comprises anode, cathode and at least one emitting layer. Apart from these layers, it may comprise further layers, in particular selected from hole-injection layer, hole-transport layer, hole-blocking layer, electron-transport layer, electron-injection layer and/or charge-generation layer (T. Matsumoto et al., *Multiphoton Organic EL Device Having Charge Generation Layer*, IDMC 2003, Taiwan; Session 21 OLED (5)). Each of these layers does not necessarily have to be present. Suitable hole-injection and hole-transport materials are, for example, aromatic amines, as usually used in accordance with the prior art, which may also be p-doped. Suitable electron-transport materials are, for example, metal-chelate complexes, for example $AlQ_3$, compounds based on electron-deficient heterocycles, for example triazine derivatives, or compounds containing aromatic carbonyls or phosphine oxides, as described, for example, in WO 05/084081 and WO 05/084082, each of which may also be n-doped. Suitable electron-injection materials are, in particular, fluorides and oxides of the alkali and alkaline earth metals, for example NaF, $BaF_2$, $CaF_2$, LiF or $Li_2O$.

The compounds of the formula (1) can be used in various functions in the organic electronic device.

In a preferred embodiment of the invention, the compound of the formula (1) is used as emitting compound in an emitting layer. The compounds of the formula (1) are particularly suitable for this function if the symbol Z stands for N and the symbols X and, if present, Y stand for $CR_2$, O, NR and/or $SiR_2$.

The compounds are preferably used in the form of a mixture with a host material. A host material is taken to mean the component in a system comprising host and dopant (binary system) that is present in the system in the higher proportion. In a system comprising a host and a plurality of dopants (ternary and higher systems), the host is taken to mean the component whose proportion is the highest in the mixture. Suitable host materials are various classes of substance, as usually used in accordance with the prior art as host materials for fluorescent organic electroluminescent devices. Preferred host materials are selected from the classes of the oligoarylenes (for example 2, 2',7,7'-tetraphenylspirobifluorene as described in EP 676461 or dinaphthylanthracene), in particular the oligoarylenes containing condensed aromatic groups, the oligoarylenevinylenes (for example DPVBi (bis-diphenylvinylbiphenyl) or spiro-DPVBi as described in EP 676461), the polypodal metal complexes (for example as described in WO 04/081017), the hole-conducting compounds (for example as described in WO 04/058911), in particular the triarylamine derivatives and the carbazole derivatives, the electron-conducting compounds, in particular ketones, phosphine oxides and sulfoxides (for example as described in WO 05/084081 and WO 05/084082), the atropisomers (for example as described in WO 06/048268), the ansa compounds (for example as described in WO 06/097208), the cycloalkylphenylanthracenes (for example as described in the unpublished application DE 102005026651.7) or the boronic acid derivatives (for example as described in WO 06/177052). Particularly preferred host materials are selected from the classes of the oligoarylenes containing naphthalene, anthracene, pyrene and/or perylene, or atropisomers of these compounds, the ketones, the phosphine oxides, the sulfoxides and the boronic acid derivatives. Very particularly preferred host materials are selected from the classes of the oligoarylenes containing anthracene and/or pyrene, or atropisomers of these compounds, and the phosphine oxides.

The proportion of the compound of the formula (1) in the mixture is between 0.1 and 99.0% by weight, preferably between 0.5 and 50.0% by weight, particularly preferably between 1.0 and 20.0% by weight, in particular between 1.0 and 10.0% by weight. Correspondingly, the proportion of the host material in the mixture is between 1.0 and 99.9% by weight, preferably between 50.0 and 99.5% by weight, particularly preferably between 80.0 and 99.0% by weight, in particular between 90.0 and 99.0% by weight.

In a further embodiment of the invention, the organic electroluminescent device has a plurality of emitting layers, where at least one of these layers comprises at least one compound of the formula (1), preferably in combination with a host material. These emission layers particularly preferably have in total a plurality of emission maxima between 380 nm and 750 nm, resulting overall in white emission, i.e. at least one further emitting compound which is able to fluoresce or phosphoresce and emits yellow, orange or red light is used in the further emitting layer(s). Particular preference is given to three-layer systems, where at least one of these layers comprises at least one compound of the formula (1), preferably in combination with a host material, and where the three layers exhibit blue, green and orange or red emission (for the basic structure see, for example, WO 05/011013).

In a further embodiment of the invention, the compound of the formula (1) is used as hole-transport and/or hole-injection material. This applies in particular if the symbol Z stands for N or P, in particular for N, and the symbols X and, if present, Y stand for $CR_2$, O, NR and/or $SiR_2$. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which lies between the hole-injection layer and the emission layer. If the compound of the formula (1) is used as hole-transport or as hole-injection material, it may be preferred for it to be doped with electron-acceptor compounds, for example with $F_4$-TCNQ or with compounds as described in EP 1476881 or EP 1596445. If the compound of the formula (1) is employed as hole-transport and/or hole-injection material in a hole-transport layer and/or a hole-injection layer, a proportion of 100%, i.e. the use of this compound as pure material, may also be preferred.

It is furthermore preferred to employ the compounds of the formula (1) as electron-transport material and/or as hole-blocking material for fluorescent and phosphorescent OLEDs and/or as triplet matrix material for phosphorescent OLEDs. This applies in particular to compounds in which the group Z stands for P=O and/or the groups X and, if present, Y stand for C=O, P=O, S=O or $SO_2$.

Preference is furthermore given to an organic electroluminescent device, characterised in that one or more layers are coated by means of a sublimation process, in which the materials are vapour-deposited in vacuum sublimation units at a pressure of less than $10^{-5}$ mbar, preferably less than $10^{-6}$ mbar, particularly preferably less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing Soluble compounds of the formula (1) are necessary for this purpose. High solubility can be achieved through suitable substitution of the compounds.

The invention furthermore relates to mixtures comprising at least one compound of the formula (1) and at least one host material.

The organic electroluminescent devices according to the invention have the following surprising advantages over the prior art:

1. The stability of the devices becomes higher compared with systems in accordance with the prior art, which is evident, in particular, from a significantly longer lifetime.
2. The compounds have higher thermal stability than stilbenamines, which are used as blue emitters in accordance with the prior art. In particular, neither thermally induced cis/trans isomerisation nor a thermally induced metathesis reaction is observed in the case of these compounds. Thus, these compounds can be sublimed virtually loss-free and without resulting in contamination in the device and enable reproducible device production.
3. The compounds exhibit a dark-blue emission colour on use in OLEDs.

The invention is explained in greater detail by the following examples, without wishing to restrict it thereby.

EXAMPLES

The following syntheses are carried out under a protective-gas atmosphere, unless indicated otherwise. The starting materials can be purchased from ALDRICH or ABCR (2-bromobiphenyl, palladium(II) acetate, tris-1-furylphosphine, inorganics, solvents). The synthesis of 10-bromo-5H-dibenzo[a,d]cyclohepten-5-one is described in the literature (B. Taljaard et al., Eur. J. Org. Chem. 2005, 12, 2607), that of 5H-dibenzo-[a,d]cycloheptene is described in the literature (C. Schmuck et al., Synthesis 2002, 5, 655) and that of 10-bro- modibenz[b,f]oxepine is described in the literature (M. Nogradi et al., Acta Chimica Academiae Scientiarum Hungaricae 1978, 96(4), 393).

Example 1

Tris(4-(10-dibenzo[a,d]cycloheptene-5-spiro-9-bifluorene)-phenyl)amine

A) 10 Bromodibenzo[a,d]cycloheptene-5-spiro-9-bifluorene

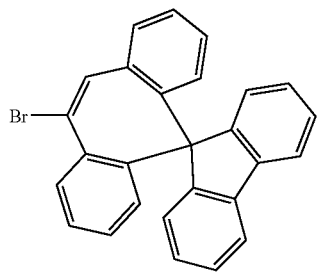

The corresponding Grignard reagent is prepared from a mixture of 49.0 ml (284 mmol) of 2-bromobiphenyl and 4.3 ml (55 mmol) of 1,2-dichloroethane in 400 ml of THF and 8.1 g (333 mmol) of magnesium. A solution of 77.0 g (270 mmol) of 10-bromo-5H-dibenzo[a,d]cyclohepten-5-one in 400 ml of THF is allowed to run rapidly into this solution with vigorous stirring, and the mixture is stirred at room temperature for a further 16 h. 20 ml of EtOH are added to the solution, the solvent is removed completely in vacuo, the residue is taken up in 1000 ml of glacial acetic acid, 5 ml of conc. hydrochloric acid are added, the mixture is refluxed for 3 h, 200 ml of toluene are then added, the mixture is allowed to cool with stirring, and the crystalline precipitate is filtered off with suction, washed three times with 100 ml of glacial acetic acid each time and three times with 100 ml of ethanol and then dried in vacuo. Yield: 102.0 g (89.6% of theory), purity about 98% according to NMR.

B) Tris(4-(10-dibenzo[a,d]cycloheptene-5-spiro-9-bifluorene)phenyl)-amine

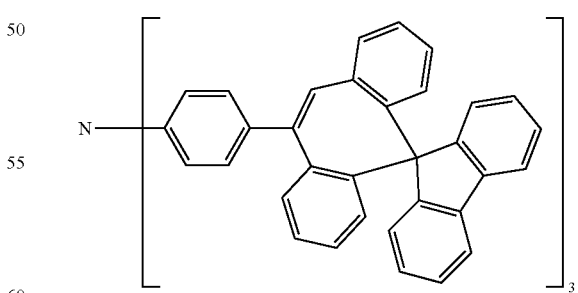

26.0 ml (65 mmol) of n-butyllithium (2.5 M in n-hexane) are added dropwise to a solution, cooled to −78° C., of 25.3 g (60 mmol) of 10-bromo-5H-dibenzo[a,d]cycloheptene-5-spiro-9-bifluorene in 600 ml of THF, and the mixture is stirred at −78° C. for a further 2 h. 8.0 ml (72 mmol) of trimethyl borate are then added, the mixture is stirred at −78° C. for a further 30 min. and warmed to 0° C. in a warm-water bath, 600 ml of dioxane, 180 ml of 1.0 M sodium carbonate solution, 8.7 g (18 mmol) of tris(4-bromophenyl)-amine, 135 mg (0.6 mmol) of palladium(II) acetate and 1.4 g (6 mmol) of tris-2-furylphosphine are added, and the mixture is refluxed for 16 h. After cooling, the precipitate is filtered off with suction, washed three times with 200 ml of water and three times with 100 ml of ethanol, dried, recrystallised five times from dioxane (about 40 ml/g) and then sublimed at T=365° C., p=5×10$^{-5}$ mbar. Yield: 9.8 g (43.2% of theory), purity 99.9% according to HPLC.

Example 2

Tris(4-(10-dibenzo[a,d]cycloheptene-5-spiro-9-(2,7-di-tertbutyl)bifluorene)phenyl)amine

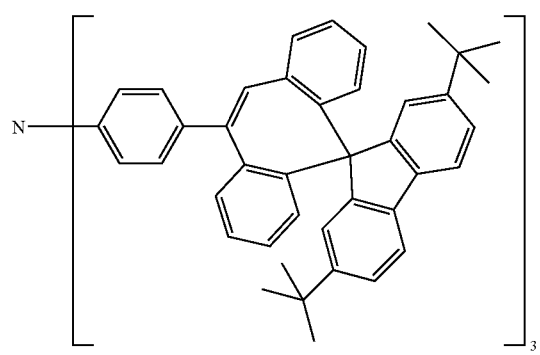

Procedure analogous to Example 1, with 2-bromobiphenyl being replaced by 98.1 g (284 mmol) of 2-bromo-4,4'-di-tert-butylbiphenyl. Sublimation at T=360° C., p=5×10$^{-5}$ mbar. Yield: 16.4 g (56.7% of theory), purity 99.9% according to HPLC.

Example 3

Diphenyl-(4-10-dibenzo[a,d]cycloheptene-5-spiro-9-bifluorene)phenyl)amine

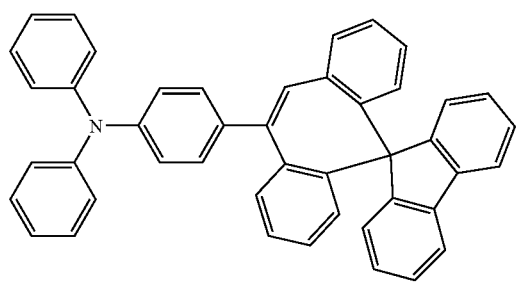

Procedure analogous to Example 1, with tris(4-bromophenyl)amine being replaced by 17.8 g (55 mmol) of diphenyl-(4-bromophenyl)amine. Recrystallisation from toluene/acetonitrile. Sublimation at T=315° C., p=5×10$^{-5}$ mbar, Yield: 22.9 g (71.0% of theory), purity 99.9% according to HPLC.

Further Examples

The following compounds are prepared analogously to Example 3 starting from the bromoarylamines shown.

| Example | Boronic acid | Product | Yield |
|---|---|---|---|
| 4 | | | 45.0% |
| 5 | | | 67.5% |

-continued

| Example | Boronic acid | Product | Yield |
|---|---|---|---|
| 6 | | | 71.8% |
| 7 | | | 73.4% |
| 8 | | | 77.7% |
| 9 | | | 65.2% |

Example 10

Tris(4-(10-(5-dimethyl)dibenzo[a,d]cycloheptene)phenyl)-amine

A) 5-Dimethyldibenzo[a,d]cycloheptene

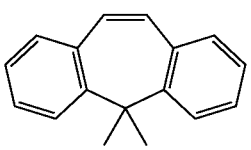

12.3 g (110 mmol) of potassium tert-butoxide are added at 10° C. to a solution of 19.2 g (100 mmol) of 5H-dibenzo[a,d]cycloheptene in 300 ml of DMSO, the mixture is stirred for 10 min., 7.2 ml (115 mmol) of methyl iodide are then added, and the mixture is stirred for a further 30 min. 12.3 g (110 mmol) of potassium tert-butoxide are subsequently added at 10° C., the mixture is stirred for 10 min., 7.2 ml (115 mmol) of methyl iodide are then added, and the mixture is stirred for a further 30 min. 500 ml of water are added, and the solid is filtered off with suction and recrystallised three times from butanol. Yield: 14.8 g (67.1% of theory), purity 95% according to NMR.

B) 10-Bromo-5-dimethyldibenzo[a,d]cycloheptene

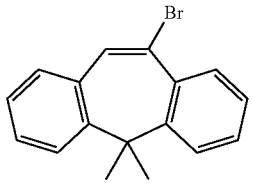

38.4 ml (750 mmol) of bromine are added dropwise to a suspension of 110.2 g (500 mmol) of 5-dimethyldibenzo[a,d]cycloheptene in 1000 ml of glacial acetic acid, and the mixture is stirred at room temperature for 16 h. The crystalline solid is filtered off with suction, washed with a little glacial acetic acid and ethanol and dried.

The solid obtained in this way is added to a solution of 60 g (1.5 mol) of sodium hydroxide in 3000 ml of methanol at 50° C. with vigorous stirring, the mixture is refluxed for 1.5 h, 1500 ml of methanol are then distilled off, the same amount of water is added, the mixture is allowed to cool, and the crystalline solid is filtered off with suction, washed three times with 200 ml of water each time and three times with 200 ml of methanol each time and dried in vacuo. Yield: 132.4 g (88.5% of theory), purity 98% according to NMR.

C) Tris(4-(10-(5-dimethyl)dibenzo[a,d]cycloheptene)phenyl)amine

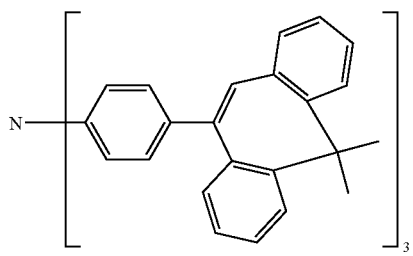

Procedure analogous to Example 1B, with 10-bromo-5H-dibenzo[a,d]-cycloheptene-5-spiro-9-bifluorene being replaced by 18.0 g (60 mmol) of 10-bromo-5-dimethyldibenzo[a,d]cycloheptene. Recrystallisation from DMF. Sublimation at T=320° C., p=5×10⁻⁵ mbar. Yield: 8.7 g (53.8% of theory), purity 99.9% according to HPLC.

Example 11

Tris(4-(10-dibenzo[b,f]oxepine)phenyl)amine

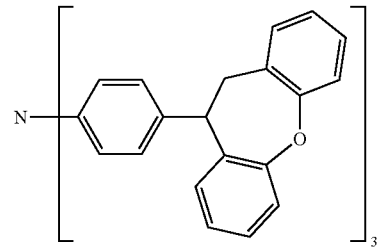

Procedure analogous to Example 1B, with 10-bromo-5H-dibenzo[a,d]-cycloheptene-5-spiro-9-bifluorene being replaced by 16.4 g (60 mmol) of 10-bromodibenzo[b,f]oxepine. Recrystallisation from NMP. Sublimation at T=310° C., p=5×10⁻⁵ mbar. Yield: 6.9 g (46.5% of theory), purity 99.9% according to HPLC.

Example 12

Comparison of the Thermal Stability

In order to compare the thermal stability of the compounds from Examples 1, 2, 3, 10 and 11 according to the invention with the open-chain styryl compound tris(4-stilben)amine [114869-94-2] in accordance with the prior art, in each case 100 mg of these compounds having a purity of 99.9% according to HPLC were melted in vacuo in ampoules and then stored at 280° C. for 100 h.

The HPLC-MS analysis shows very good thermal stability of the compounds from Examples 1, 2, 3, 10 and 11 according to the invention, which exhibit no significant change. By contrast, the comparative compound tris(4-stilben)amine undergoes substantial decomposition; under the conditions described, only about 25% of tris(4-stilbene)amine can be detected after 100 h. Besides oligomeric fractions, principally 4,4'-di-tert-butylstilbene forms.

Example 13

Production of OLEDs

OLEDs are produced by a general process as described in WO 04/058911, which is adapted in individual cases to the particular circumstances (for example layer thickness variation in order to achieve optimum efficiency or colour).

The results for various OLEDs are presented in Examples 14 to 21 below. Glass plates coated with structured ITO (indium tin oxide) form the substrates of the OLEDs. For better processing, PEDOT (spin-coated from water; purchased from H. C. Starck, Goslar, Germany; poly(3,4-ethylene-dioxy-2,5-thiophene)) is applied directly to the substrate. The OLEDs always consist of the following layer sequence: substrate/PEDOT 20 nm/-hole-injection layer (HIL1) 20 nm/hole-transport layer (HTM1) 20 nm/emission layer (EML) 30 nm/electron-transport layer (ETM1) 20 nm and finally a cathode. The materials apart from PEDOT are thermally vapour-deposited in a vacuum chamber. The EML here always consists of a matrix material (host) and a dopant (guest), which is admixed with the host by coevaporation. The host material used is host H1. The cathode is formed by a 1 nm thin LiF layer and a 150 nm Al layer deposited on top. Table 1 shows the chemical structures of the materials used to construct the OLEDs.

These OLEDs are characterised by standard methods; for this purpose, the electroluminescence spectra, the efficiency (measured in cd/A), the power efficiency (measured in lm/W) as a function of the brightness, calculated from current/voltage/luminance characteristics (IUL characteristics), and the lifetime are determined. The lifetime is defined as the time after which the initial luminance has dropped from 1000 cd/m$^2$ to half.

Table 2 shows the results for some OLEDs (Examples 14 to 21).

TABLE 1

Materials used

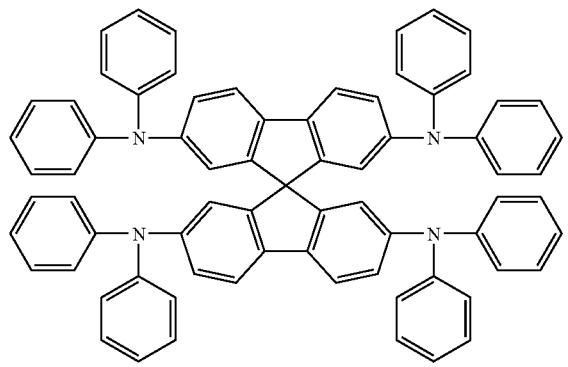

HIL1

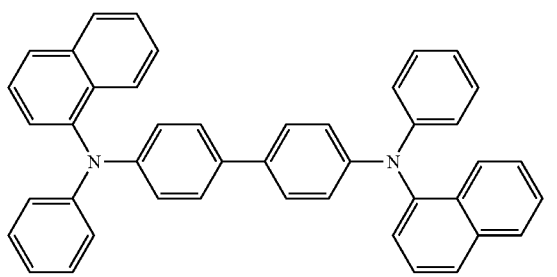

HTM1

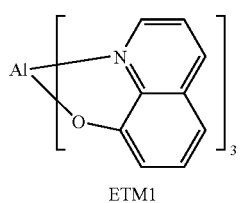

ETM1

TABLE 1-continued

Materials used

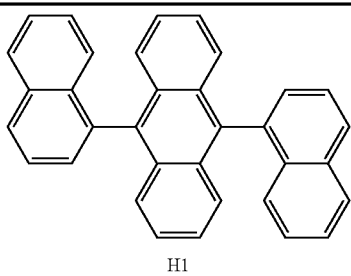

H1

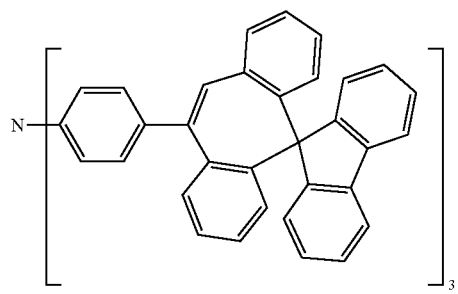

D1 (Example 1)

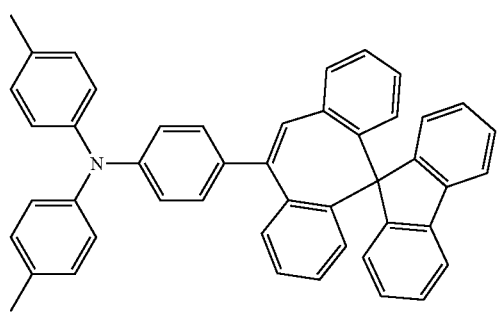

D4 (Example 4)

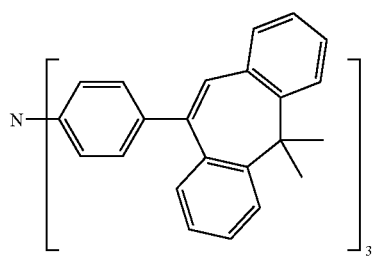

D10 (Example 10)

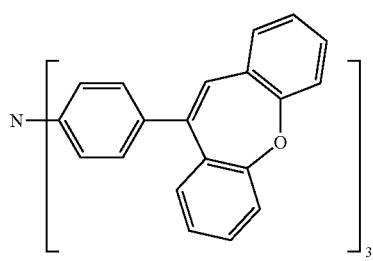

D11 (Example 11)

TABLE 2

| Results for some OLEDs | | | | | |
|---|---|---|---|---|---|
| Ex. | EML | Max. efficiency (cd/A) | Voltage (V) at 1000 cd/m² | CIE | Lifetime (h) at 1000 cd/m² |
| 14 | H1 + 5% D1 | 6.5 | 5.6 | x = 0.17/y = 0.19 | 2200 |
| 15 | H1 + 3% D1 | 6.3 | 5.7 | x = 0.16/y = 0.18 | 1800 |
| 16 | H1 + 5% D4 | 10.5 | 5.5 | x = 0.18/y = 0.21 | 2400 |
| 17 | H1 + 3% D4 | 3.8 | 5.8 | x = 0.18/y = 0.20 | 2000 |
| 18 | H1 + 5% D10 | 6.2 | 5.5 | x = 0.17/y = 0.18 | 2300 |
| 19 | H1 + 3% D10 | 6.1 | 5.7 | x = 0.16/y = 0.18 | 2100 |
| 20 | H1 + 5% D11 | 12.5 | 5.4 | x = 0.18/y = 0.45 | 8100 |
| 21 | H1 + 7% D11 | 13.5 | 5.3 | x = 0.18/y = 0.46 | 8500 |

The invention claimed is:

1. A compound of formula (1)

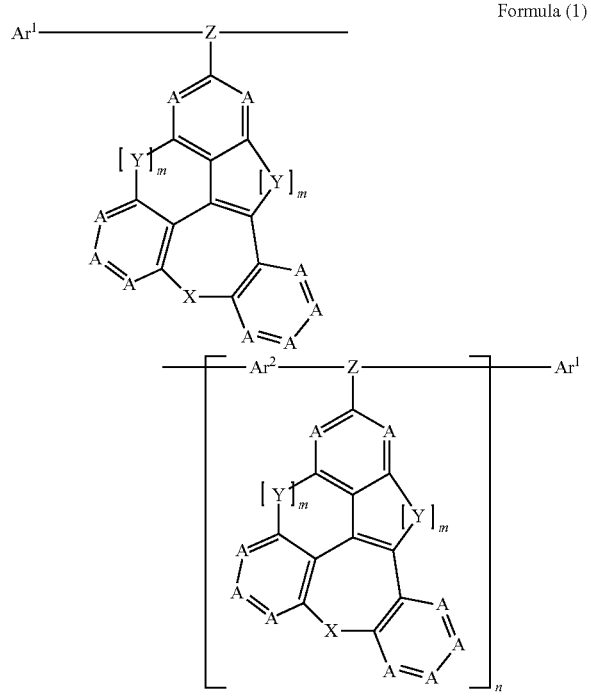

Formula (1)

wherein

Z is, identically or differently on each occurrence, N, P, As, or P=O;

X and Y are, identically or differently on each occurrence, $CR_2$, C=O, O, S, NR, $SiR_2$, PR, P(=O)R, S(=O), or $SO_2$;

A is, identically or differently on each occurrence, CR or N;

$Ar^1$ is, identically or differently on each occurrence, a monovalent aromatic or heteroaromatic ring system having 5 to 40 aromatic ring atoms optionally substituted by one or more radicals R;

$Ar^2$ is, identically or differently on each occurrence, a divalent aromatic or heteroaromatic ring system having 5 to 40 aromatic ring atoms optionally substituted by one or more radicals R;

R is, identically or differently on each occurrence, H; F; Cl; Br; I; CN; $NO_2$; $Si(R^1)_3$; $N(R^1)_2$; $B(OR^1)_2$; a straight-chain alkyl, alkoxy or thioalkoxy group having 1 to 40 C atoms optionally substituted by one or more radicals $R^1$; a branched or cyclic alkyl, alkoxy or thioalkoxy group having 3 to 40 C atoms optionally substituted by one or more radicals $R^1$; wherein one or more non-adjacent $CH_2$ groups of said straight-chain alkyl, alkoxy or thioalkoxy groups or said branched or cyclic alkyl, alkoxy or thioalkoxy groups are optionally replaced by —$R^1$C=$CR^1$—, —C=C—, $Si(R^1)_2$, $Ge(R^1)_2$, $Sn(R^1)_2$, C=O, C=S, C=Se, C=$NR^1$, —O—, —S—, —$N(R^1)$— or —$CONR^1$— and wherein one or more H atoms of said straight-chain alkyl, alkoxy or thioalkoxy groups or said branched or cyclic alkyl, alkoxy or thioalkoxy groups are optionally replaced by F, Cl, Br, I, CN, or $NO_2$; an aromatic or heteroaromatic ring system having 5 to 40 aromatic ring atoms optionally substituted by one or more radicals; an aryloxy or heteroaryloxy group having 5 to 24 aromatic ring atoms optionally substituted by one or more radicals; or a combination of two, three, four, or five of these systems; and wherein two or more substituents R optionally define a mono- or poly cyclic, aliphatic or aromatic ring system with one another;

R is, identically or differently on each occurrence, H or a hydrocarbon radical having 1 to 20 C atoms, which may be aliphatic or aromatic or a combination of aliphatic and aromatic, wherein one or more H atoms are optionally replaced by F, and wherein two or more radicals $R^1$ optionally define a mono- or polycyclic, aliphatic or aromatic ring system with one another;

n is 0, 1, 2, or 3;

m is, identically or differently on each occurrence, 0 or 1, wherein when m=0, Y is not present and instead radicals R are bonded in these positions.

2. The compound of claim 1, wherein Z is, identically or differently on each occurrence, N or P=O.

3. The compound of claim 1, wherein no more than one A in each aromatic ring is N.

4. The compound of claim 1, wherein at least one group $Ar^1$ is a group of formula (2)

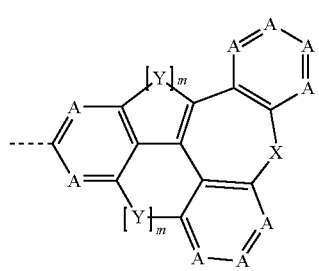

Formula (2)

wherein ---- is the bond to Z.

5. The compound of claim 1, wherein said compound is a compound of formula (1a)

Formula (1a)

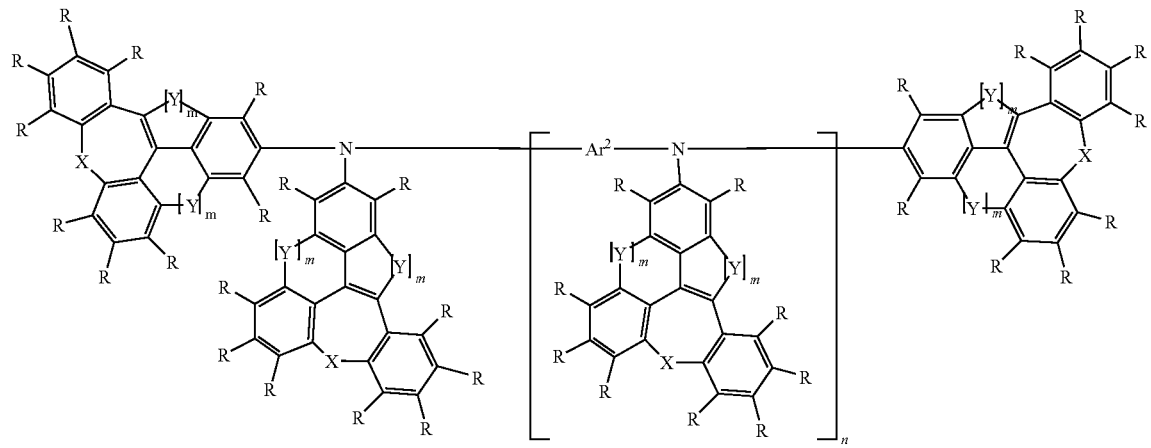

6. The compound of claim 1, wherein X is, identically or differently on each occurrence, $CR_2$, O, NR, or $SiR_2$.

7. The compound of claim 1, wherein X is $CR_2$, wherein R is, identically or differently on each occurrence, a straight-chain alkyl group having 1 to 4 C atoms wherein one or more H atoms is optionally replaced by F, a branched alkyl group having 3 or 4 C atoms wherein one or more H atoms is optionally replaced by F, an aryl or heteroaryl group having 5 to 10 aromatic ring atoms, or a combination of two or three of these systems; and wherein both R in $CR_2$ optionally define a mono- or polycyclic, aliphatic or aromatic ring system with one another.

8. The compound of claim 1, wherein Y is, identically or differently on each occurrence, $CR_2$, O, NR, or $SiR_2$.

9. The compound of claim 1, wherein said compound is a compound of formula (1b)

Formula (4)

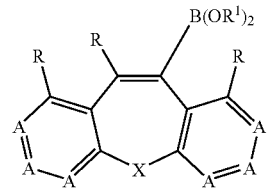

in a Suzuki coupling with the central unit of a compound of formula (1) which contains chlorine, bromine, iodine, triflate, tosylate, or $OSO_2R^1$ as a reactive group, wherein X, A, R, and $R^1$ is as defined in claim 1.

15. An organic electronic device comprising at least one compound of claim 1.

Formula (1b)

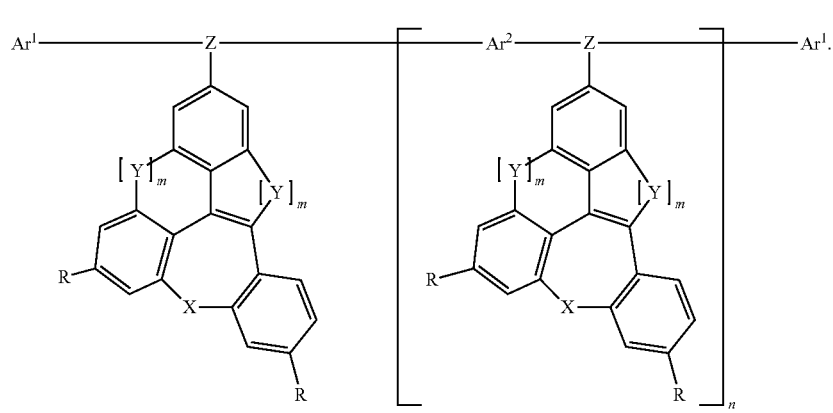

10. The compound of claim 1, wherein n is 0, 1, or 2.

11. The compound of claim 1, wherein m is 0.

12. The compound of claim 1, wherein said compound has a three-fold axis of symmetry.

13. A polymer, oligomer, or dendrimer comprising one or more compounds of claim 1, wherein one or more radicals R bond said compound to said polymer, oligomer, or dendrimer.

14. A process for preparing the compound of claim 1, comprising reacting a boronic acid derivative of formula (4)

16. An organic electronic device comprising at least one organic layer which comprises at least one compound of claim 1.

17. The organic electronic device of claim 16, wherein said organic electronic device is selected from the group consisting of organic electroluminescent devices, organic field-effect transistors, organic thin-film transistors, organic light-emitting transistors, organic integrated circuits, organic solar cells, organic field-quench devices, organic photo receptors, light-emitting electrochemical cells, and organic laser diodes.

18. The organic electronic device of claim 17, wherein said organic electronic device comprises an anode, a cathode, at least one emitting layer, and optionally at least one further layer selected from the group consisting of hole-injection layers, hole-transport layers, hole-blocking layers, electron-transport layers, electron-injection layers, and charge-generation layers.

19. The organic electronic device of claim 18, wherein the compound of claim 1 is used as an emitting compound in an emitting layer and/or as a hole-transport or hole-injection material and/or as a electron-transport material and/or as a hole-blocking material for fluorescent or phosphorescent organic electroluminescent devices and/or as a triplet matrix material for phosphorescent organic electroluminescent devices.

20. A mixture comprising at least one compound of claim 1 and at least one host material.

* * * * *